（12) United States Patent
Feith et al.

(10) Patent No.: US 10,724,647 B2
(45) Date of Patent: Jul. 28, 2020

(54) CHECK VALVES

(71) Applicant: CareFusion 303, Inc., San Diego, CA (US)

(72) Inventors: Raymond Feith, Chino Hills, CA (US); Siddarth K. Shevgoor, Laguna Beach, CA (US); Eugene Mason, La Habra Heights, CA (US); Mark Kaplan, Raleigh, NC (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 15/952,074

(22) Filed: Apr. 12, 2018

(65) Prior Publication Data

US 2019/0316695 A1  Oct. 17, 2019

(51) Int. Cl.
*F16K 15/14* (2006.01)
*B01D 29/56* (2006.01)
*B01D 35/153* (2006.01)
*B01D 29/11* (2006.01)

(52) U.S. Cl.
CPC ............ *F16K 15/14* (2013.01); *B01D 29/112* (2013.01); *B01D 29/56* (2013.01); *B01D 35/153* (2013.01); *F16K 15/148* (2013.01); *B01D 2201/167* (2013.01)

(58) Field of Classification Search
CPC ....... F16K 15/148; F16K 15/14; B01D 29/56; B01D 2201/167
See application file for complete search history.

(56) References Cited

U.S. PATENT DOCUMENTS

2010/0300556 A1   12/2010   Carmody et al.

FOREIGN PATENT DOCUMENTS

| DE | 9319810 U1 | 2/1994 | |
|---|---|---|---|
| DE | 202006016730 U1 | 1/2007 | |
| EP | 0170007 A2 * | 2/1986 | ........... F16K 15/148 |
| EP | 0887085 A2 | 12/1998 | |
| EP | 1946793 A1 | 7/2008 | |
| WO | WO-2010107597 A1 | 9/2010 | |
| WO | WO-2015109306 A1 | 7/2015 | |

OTHER PUBLICATIONS

International Search Report and Written Opinion for Application No. PCT/US2019/025772, dated Jul. 24, 2019, 15 pages.

* cited by examiner

*Primary Examiner* — P. Macade Nichols
(74) *Attorney, Agent, or Firm* — Morgan, Lewis & Bockius LLP (57) ABSTRACT

A check valve includes an upper housing having an inlet of the check valve, a lower housing axially coupled to the upper housing and having an outlet of the check valve, a valve portion cooperatively formed by the upper and lower housings, a passageway extending between the inlet and outlet, a first filter included in the upper housing to limit passage of undesirable matter in fluid flowing through the check valve, a second filter included in the lower housing to limit passage of undesirable matter in fluid flowing through the check valve, each of the first filter and the second filter including a plurality of vertical structures disposed in the valve portion and extending axially and radially in the valve portion, and a valve member positioned in the valve portion to selectively permit fluid to flow through the check valve.

18 Claims, 5 Drawing Sheets

CHECK VALVES

BACKGROUND

Field

Embodiments disclosed are related to check valves, and more particularly to check valves having filtering mechanisms for filtering particulate matter in fluid flowing through the check valve.

Description of Related Art

Patients are commonly injected with IV solutions that are initially provided in an IV reservoir (a bottle or bag) and dripped into the vein of the patient through an IV line. Typically, an injection port is provided along the IV line and adapted to function with a syringe to permit an injectate to be added to the IV solution. A check valve is also commonly included in the IV line to permit fluid flow only in the direction of the patient. This ensures that the injectate flows downstream toward the patient, not upstream toward the IV reservoir.

SUMMARY

An aspect of the present disclosure provides a check valve including an upper housing having an inlet of the check valve; a lower housing having an outlet of the check valve; a valve portion formed by the upper and lower housings; a passageway extending between the inlet and outlet; a first filter in the upper housing to limit passage of undesirable matter in fluid flowing through the check valve, the first filter extending axially and radially in the valve portion; and a valve member arranged in the valve portion to selectively permit fluid to flow through the check valve.

Another aspect of the present disclosure provides a check valve including an upper housing having an inlet of the check valve; a lower housing axially coupled to the upper housing and having an outlet of the check valve; a valve portion cooperatively formed by the upper and lower housings; a passageway extending between the inlet and outlet; a first filter included in the upper housing to limit passage of undesirable matter in fluid flowing through the check valve; a second filter included in the lower housing to limit passage of undesirable matter in fluid flowing through the check valve, each of the first filter and the second filter including a plurality of vertical structures disposed in the valve portion and extending axially and radially in the valve portion; and a valve member positioned in the valve portion to selectively permit fluid to flow through the check valve.

Yet another aspect of the present disclosure provides a check valve including an upper housing having an inlet of the check valve; a lower housing axially coupled to the upper housing and having an outlet of the check valve; a valve portion cooperatively formed by the upper and lower housings; a passageway extending between the inlet and outlet; and a valve member arranged in the valve portion to selectively permit fluid to flow through the check valve. The upper housing defines an opening in fluid communication with the valve portion, and the valve member is elongated and has a first end coupled to the lower housing and the upper housing, and a second opposite end occluding the opening.

Still another aspect of the present disclosure provides a check valve including an upper housing having an inlet of the check valve; a lower housing axially coupled to the upper housing and having an outlet of the check valve; a valve portion formed by the upper and lower housings; a passageway extending between the inlet and outlet; and a valve member arranged in the valve portion to selectively permit fluid to flow through the check valve. The lower housing includes a plurality projections extending of axially and radially from an internal surface of the lower housing in the valve portion, a flow channel is defined between adjacent projections, the flow channel being in fluid communication with the passageway and the valve portion, and the upper housing and the lower housing co-operatively define an internal cavity in the valve portion, and a radially outermost portion of the internal cavity defines a lodging space configured to retain undesirable matter in fluid.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1A:
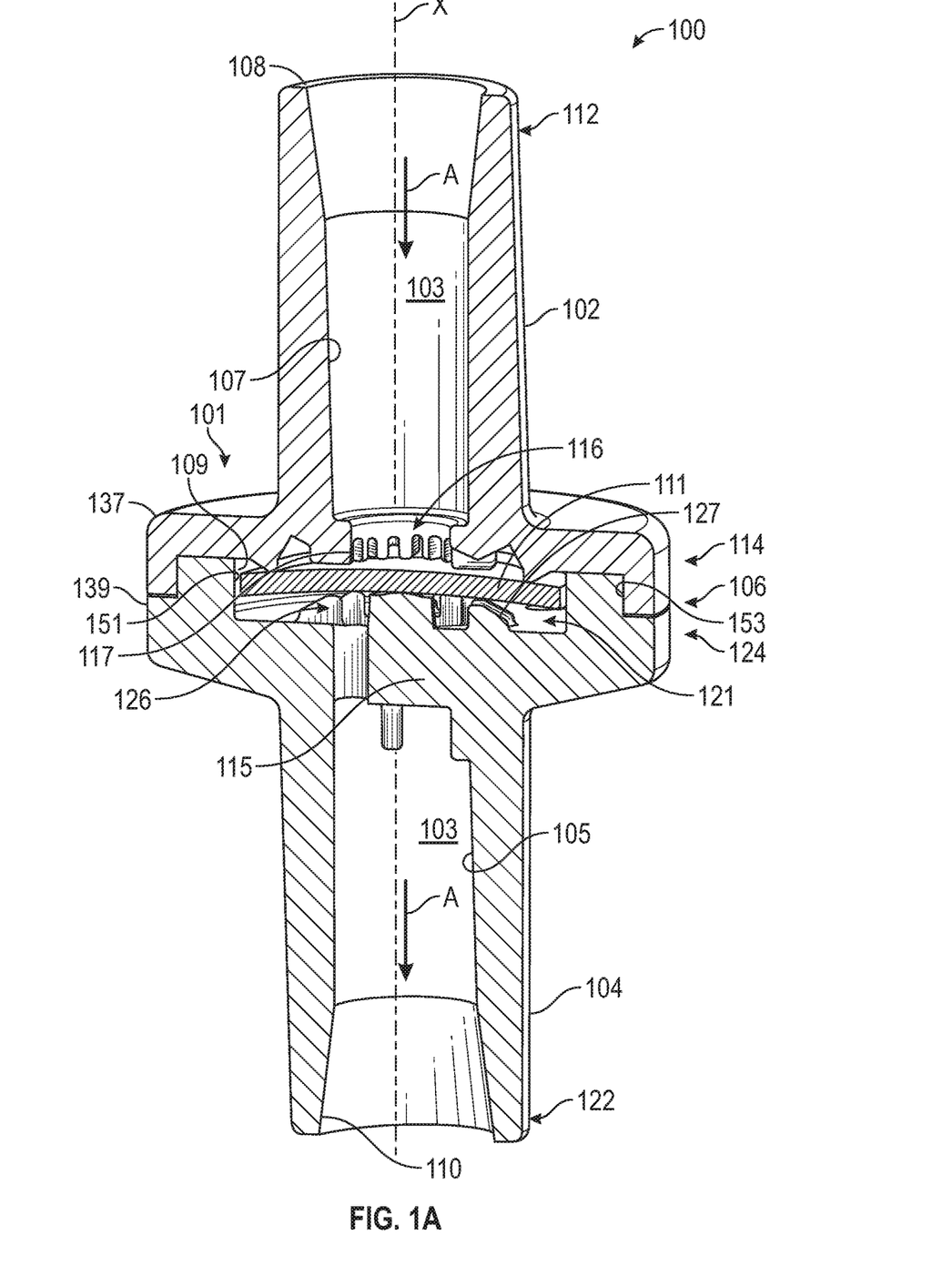
FIG. 1A is a cross-sectional view of a check valve, in accordance with aspects of the present disclosure.

FIG. 1A is a cross-sectional view of a check valve 100, in accordance with aspects of the present disclosure. Herein, the cross-sectional view of the check valve 100 in FIG. 1A is rotated about its axis to more clearly illustrate some of the features of the check valve 100. Referring to FIG. 1A, the check valve 100 includes an axially extending body 101 defining a longitudinal axis X. The body 101 may be a generally cylindrical (or tubular) structure and may include an upper housing 102 and a lower housing 104. The upper housing 102 may include a first end 112 and an axially opposite second end 114. As illustrated, a radial extent of the upper housing 102 at the second end 114 may be greater than the radial extent thereof at the first end 112. The lower housing 104 may include a first end 122 and an axially opposite second end 124. Similar to the upper housing 102, a radial extent of the lower housing 104 at the second end 124 may be greater than the radial extent thereof at the first end 122. The respective second ends 114 and 124 of the upper housing 102 and the lower housing 104 axially contact each other to co-operatively form a valve portion 106 of the check valve 100.

The upper housing 102 may include an inlet 108 of the check valve 100 at the first end 112 and the lower housing 104 may include an outlet 110 of the check valve 100 at the first end 122. The upper housing 102 may include a flange 137 at an axial end thereof opposite the inlet 108 and the lower housing 104 may include a flange 139 at an axial end thereof opposite the outlet 110. The flanges 137 and 139 may co-operatively define the valve portion 106. The body 101 may define an internal passageway 103 axially extending between the inlet 108 and the outlet 110 and in fluid communication therewith. As is understood, the check valve 100 may permit fluid to flow (indicated by arrow A) from the inlet 108 to the outlet 110, and minimize, or otherwise limit, fluid flow from the outlet 110 to the inlet 108.

The valve portion 106 may define an internal cavity (or chamber) 121 and a flat pliable valve member 111 may be disposed in the cavity 121. More specifically, the cavity 121 may be at least partially defined by an internal vertical surface 151 of the flange 139. Alternatively, in other embodiments, the cavity 121 may be at least partially defined by an internal vertical surface 153 of the flange 137. In still other embodiments, the cavity 121 may be at least partially defined by the internal vertical surfaces 151 and 153. The valve member 111 may be a disk, plate, a diaphragm or similar, and may be square, rectangular, circular, elliptical, oblong, and the like. The shape and size of the valve member 111 is not limited to any particular shape or size. The valve member 111 may have any size and shape that may permit the valve member 111 to flex or bend under fluid pressure and permit forward flow of the fluid (from the inlet 108 to the outlet 110) through the valve 100, and occlude reverse flow of the fluid (from the outlet 110 to the inlet 108) through the valve 100.

The valve member 111 may be supported on a pedestal (or post) 115 of the lower housing 104 and may be spaced from the lower housing 104 by a gap 109. As illustrated in FIG. 1A, the pedestal 115 may be coupled to the internal sidewall 105 of the lower housing 104 and extend into the cavity 121. As discussed below, the cavity 121 may form a part of the passageway 103 and therefore, fluid flowing from the inlet 108 to the outlet 110 may flow via the cavity 121.

At the second end 114, the upper housing 102 may include a filter 116 arranged in the passageway 103. In an example and as illustrated, the filter 116 may include an array of vertical structures 117 coupled to the internal sidewall 107 of the passageway 103 and arranged about the passageway 103 at the second end 114. In an example and as illustrated, the array of vertical structures 117 may be or include an array of fins and adjacent vertical structures 117 may be spaced about 0.010 inches apart. However, the spacing between the vertical structures 117 is not limited thereto and may be increased or decreased as required by application and design. The vertical structures 117 may filter grit, or other undesirable particulate matter from the fluid flowing through the check valve 100 from the inlet 108 to the outlet 110. The vertical structures 117 may be disposed in the passageway 103 and the cavity 121 and may extend axially and radially in the passageway 103 and the cavity 121. In an example, the vertical structures 117 may protrude axially a certain distance into the cavity 121 from the internal sidewall 107 and extend a certain distance radially (inward and outward) in the cavity 121.

Another filter 126 may be arranged about the passageway 103 in the lower housing 104 at the second end 124. In an example and as illustrated, the filter 126 may also include an array of vertical structures 127 extending axially and radially and coupled to the internal sidewall 105. The vertical structures 127 may extend axially and radially a certain distance from the internal sidewall 105 and into the cavity 121. In an example, adjacent vertical structures 127 may be spaced about 0.010 inches apart. However, the spacing between the vertical structures 127 is not limited thereto. The vertical structures 127 may filter grit or other undesirable particulate matter from the fluid flowing from the cavity 121 into the passageway 103 (and flow channels 146, see below). As illustrated, the pedestal 115 may be positioned centrally in the array of vertical structures 127.

Figure 1B:
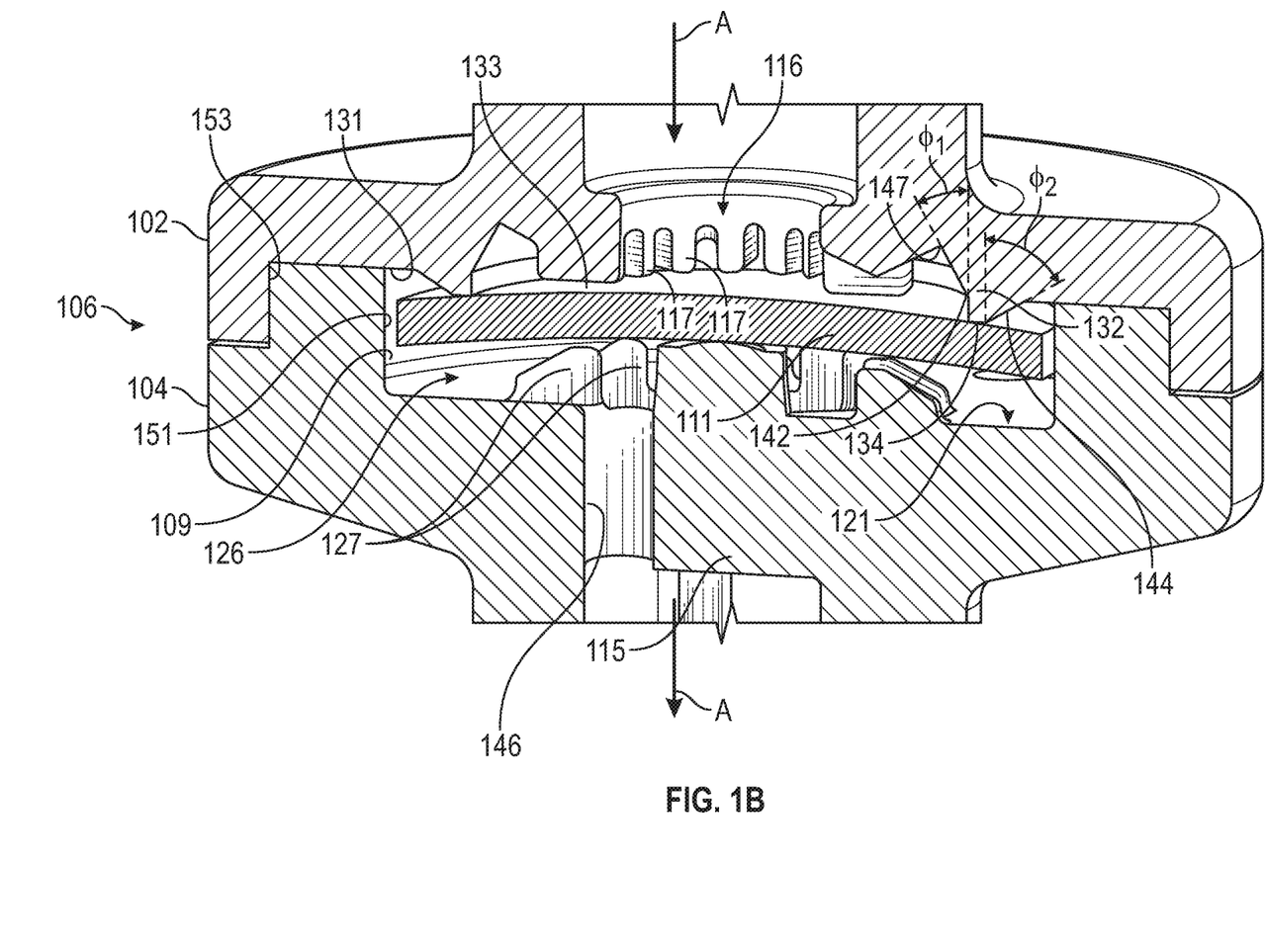
FIG. 1B illustrates the valve portion of the check valve of FIG. 1A in greater detail.

FIG. 1B illustrates the valve portion 106 in greater detail. The cavity 121 may be at least partially defined by an internal surface 131 of the upper housing 102 that extends radially outward from the internal sidewall 107. The internal surface 131 may include a projection 132 that may extend into the cavity 121 from the internal surface 131 and may be disposed around the vertical structures 117 in a circular manner. In an example, the projection 132 may define a sealing surface 134 at a distal end thereof. The projection 132 and therefore the sealing surface 134 may be disposed like a ring around the vertical structures 117. During operation, the valve member 111 may contact the sealing surface 134 to minimize or limit the fluid flow in the reverse direction, from the outlet 110 to the inlet 108.

As illustrated, the projection 132 may be formed by an upstream sidewall 142 and a downstream sidewall 144. The upstream sidewall 142 may define an angle φ1 with respect to the longitudinal axis X and the downstream sidewall 144 may define an angle φ2 with respect to the longitudinal axis X. The angle φ1 may be less than angle φ2. Stated otherwise, the upstream sidewall 142 may be more vertically disposed (less slope) than the downstream sidewall 144. As a result, the fluid, the upstream sidewall 142 may cause the fluid to swirl (a flow eddy is generated) when it contacts the upstream sidewall 142 while flowing from the inlet 108 to the outlet 110. The swirling of the fluid may divert grit and similar undesirable particulate matter that passes through the vertical structures 117 up and away from the sealing surface 134 and the grit may be lodged or otherwise trapped in the recess 147.

A plurality of channels 146 (one shown) may be included in the lower housing 104 between the internal sidewall 105 and the pedestal 115. In example, 3 channels 146 may be included in the lower housing 104. However, the number of channels 146 is not limited thereto and may be increased or decreased as required by application and design.

During assembly, the valve member 111 may be positioned on the pedestal 115 and the upper housing 102 may be lowered onto the lower housing 104. The sealing surface 134 may contact the valve member 111 adjacent the outer edge thereof. This may cause the valve member 111 to bend at the outer edges and create a normally-closed state of the check valve 100. In the assembled state, a gap 133 smaller than the spacing between the vertical structures 117 may be defined between the vertical structures 117 and upper surface of the valve member 111. This gap 133 permits the fluid to flow while limiting the size of grit or other undesirable particulate matter that passes downstream.

During operation, fluid may enter the check valve 100 via the inlet 108, flow through the passageway 103, past the vertical structures 117, and into the cavity 121. Any grit or other undesirable particulate matter larger in size than the spacing between the vertical structures 117 may be prevented from passing downstream. Also, fluid may flow between the vertical structures 117 and the upper surface of the valve member 111 and the gap therebetween may further prevent grit from flowing downstream. As mentioned above, the fluid flow may cause swirling of the fluid when the flow contacts the upstream sidewall 142 and any grit that is not filtered by the gap may be trapped in the recess 147. During normal forward flow operation, fluid flows through a gap formed between the sealing surface 134 and the upper surface of the valve member 111 due to the bending of the valve member 111. The fluid may then flow through the gap 109, the vertical structures 127, the one or more channels 146, into the passageway 103 in the lower housing 104, and exit the check valve 100 via the outlet 110. Because in the normally-closed state of the check valve 100, the disk 11 contacts the sealing surface 134, fluid flow from the outlet 110 to the inlet 108 is limited. In the event that fluid flows in the reverse direction from the outlet 110 to the inlet 108, the vertical structures 127 may prevent grit or other undesirable particulate matter from flowing into the cavity 121.

In another embodiment, the gap between adjacent vertical structures 117 (and 127, similarly) may be absent. Accordingly, instead of the array of vertical structures 117, the check valve 100 may include a circular lip or protrusion at the second end 114, wherein a gap is defined between the circular lip and the upper surface of the valve member 111. The gap may function as a filter to prevent grit from flowing into the cavity 121.

Figure 2:
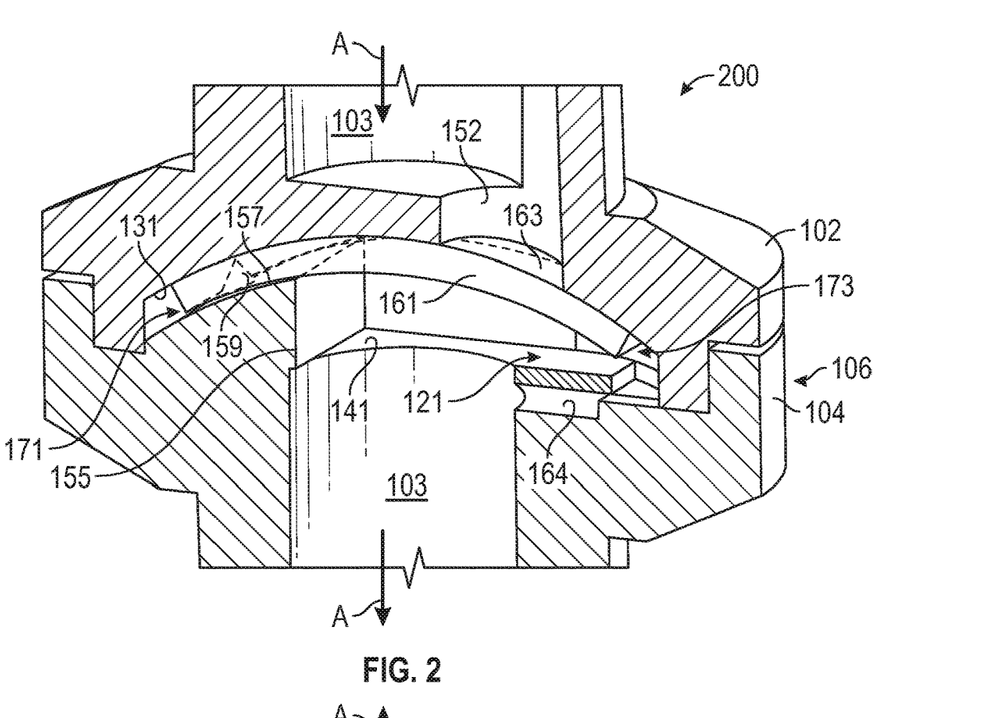
FIG. 2 is a cross-sectional view of the valve portion of another check valve, in accordance with aspects of the present disclosure.

FIG. 2 is a cross-sectional view of the valve portion 106 of a check valve 200, in accordance with aspects of the present disclosure. The check valve 200 may be similar in some respects to the check valve 100 in FIGS. 1A and 1B, and therefore may be best understood with reference thereto where like numerals designate like components not described again in detail.

As illustrated, the internal surface 131 of the upper housing 102 may define an opening 152 that is in fluid communication with the passageway 103 of the upper housing 102. In an example and as illustrated, a size (e.g., a radial extent) of the opening 152 may be smaller than the size of the passageway 103. The cavity 121 may be at least partially defined by an angled internal surface 141 of the lower housing 104 that extends radially outward from the internal sidewall 105. Thus, as illustrated, the internal surface 131 may form the top (or roof) of the cavity 121 while the internal surface 141 may form the bottom (or floor) of the cavity 121. The lower housing 104 may include a projection 155 that extend axially from the internal surface 141 towards the inlet 108 (FIG. 1A). The top surface 157 of the projection 155 may be curved and relatively flat. One or more (one shown) protrusions 159 may be disposed on the top surface 157 and extending axially in the direction of the inlet 108. The protrusions 159 may be used to align a valve member 161 (see below) and limit movement thereof. In an example, the valve member may be plate (or a diaphragm or similar) having an oblong shape (e.g., having semicircular ends connected by parallel longitudinal edges.). The plate may be flexible or pliable such that the plate selectively occludes fluid flow in the check valve 200. In an example, the protrusions 159 may be shaped as spikes. However, the protrusions 159 may have other shapes such as studs or any other shape that may limit movement of the valve member 161.

A valve member 161 may be positioned on the internal surface 141. In detail, and as illustrated, the valve member 161 may have a curvature that may correspond to the curvature of the internal surface 131. The lower surface of the valve member 161 may include holes, recesses, or similar (not illustrated) at or adjacent at a stationary end 171 of the valve member 161 for receiving the protrusions 159 therein.

In an assembled state, the valve member 161 may be positioned on the top surface 157 such that the protrusions 159 are received into the holes in the lower surface of the disk and the upper housing 102 contacts a top surface 163 of the valve member 161. The protrusions 159 ensure that the valve member 161 is retained between the upper housing 102 and the lower housing 104. The valve member 161 may extend in the cavity 121 while contacting the internal surface 131. In the normally-closed state of the check valve 200, the valve member 161 may cover the opening 152 and overlie the passageway 103 in the lower housing 104. Because the valve member 161 covers the opening 152, flow of fluid in the reverse direction, from the outlet 110 to the inlet 108, is limited.

Although discussed as being oblong, the shape and size of the valve member 161 is not limited to any particular shape or size. The valve member 161 may be sized and shaped such that the valve member 161 may flex or bend under fluid pressure to permit forward flow (from the inlet 108 to the outlet 110) of the fluid into the cavity 121 via the opening 152, cover the opening 152 to limit fluid flow in the reverse direction, and overlie the passageway 103 in the lower housing 104.

During operation, fluid may enter the check valve 200 from the inlet 108. The fluid pressure may cause the valve member 161 to bend downwards (towards the outlet 110) and a gap may be created between the internal surface 131 and the valve member 161 (more specifically, the top surface 163 of the valve member 161). Fluid may flow via the gap into the cavity 121. The cavity 121 may be in fluid communication with the passageway 103 in the lower housing 104 and the fluid may then exit the check valve 200 through the outlet 110.

Because the valve member 161 is attached to the lower housing 104 at the stationary end 171, the valve member 161 may exhibit a "springboard" type action, wherein the mobile end 173 of the valve member 161 diametrically opposite the coupled end bends in response to fluid flow (and pressure). Furthermore, because the top surface 163 of the valve member 161 contacts the internal surface 131 of the upper housing 102 during the normally-closed state of the check valve 200, fluid flow in the reverse direction is limited.

In a typical operation, the valve member 161 may bend to create the gap for fluid to flow. More specifically, a flow channel 164 may be defined in the internal surface 141 below the opening 152 and adjacent the mobile end 173 of the valve member 161. The flow channel 164 may "pull" the valve member 161 to open via vacuum pressure as the valve member 161 approaches the floor of the cavity 121. In the event the valve member 161 contacts the floor of the cavity 121, the flow channel 164 may maintain fluid flow through the check valve 200. In an example and as illustrated, the flow channel 164 may be a recess defined in the internal surface 141.

In an embodiment, the check valve 200 may include the filter 126 arranged about the opening 152. For instance, referring to FIG. 1B, the array of vertical structures 127 may be arranged about the opening 152 to filter grit or other undesirable particulate matter and limit the passage thereof into the cavity 121. In another embodiment, another filter (for example, a filter similar to filters 126 or 116) may be arranged in the cavity 121 to filter grit or other undesirable particulate matter present in the cavity 121.

As is known, check valves are normally closed devices and permit fluid flow in a forward direction (from the inlet to the outlet) and limit fluid flow in the reverse direction (from the outlet to the inlet). During low flow conditions, the fluid flow (or pressure) may not be sufficient to open the valve (e.g., deflect the valve members 111 and 161) such that grit (or other undesirable particulate matter) may pass through the gap. In such conditions, the grit may get lodged in the gap and the valve may not completely close when the fluid flow (more specifically, the forward fluid flow) stops. This causes the check valve to "weep", wherein fluid flows through the valve in the reverse direction making the check valve ineffective.

Figure 3A:
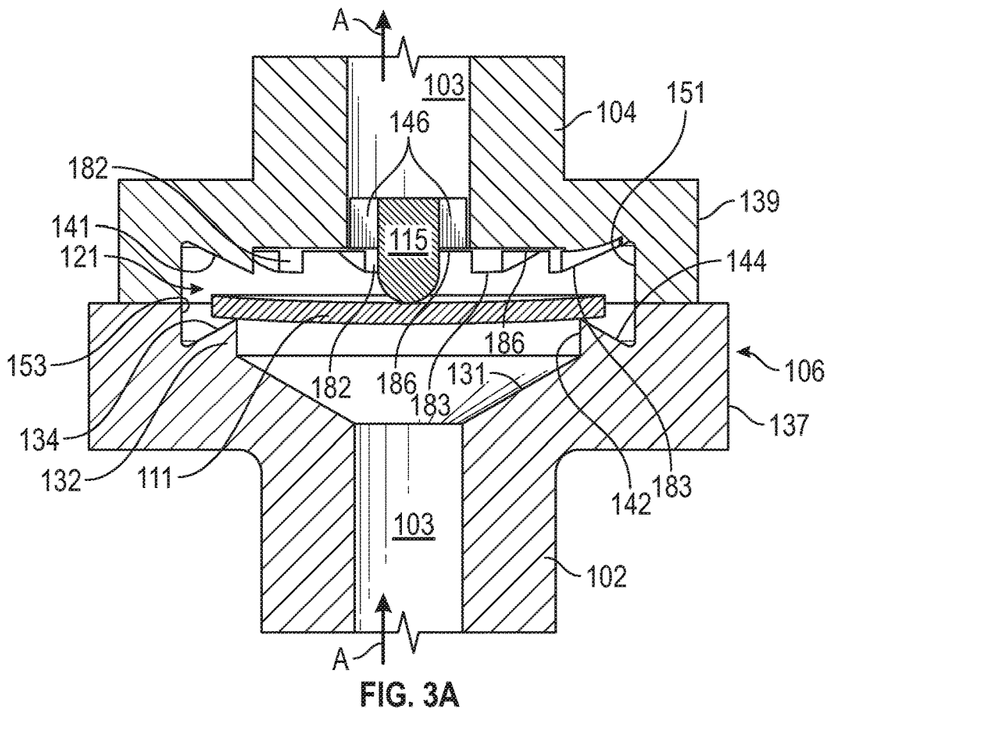
FIGS. 3A and 3B are cross-sectional views of the valve portion of another check valve, in accordance with aspects of the present disclosure.
Figure 3B:
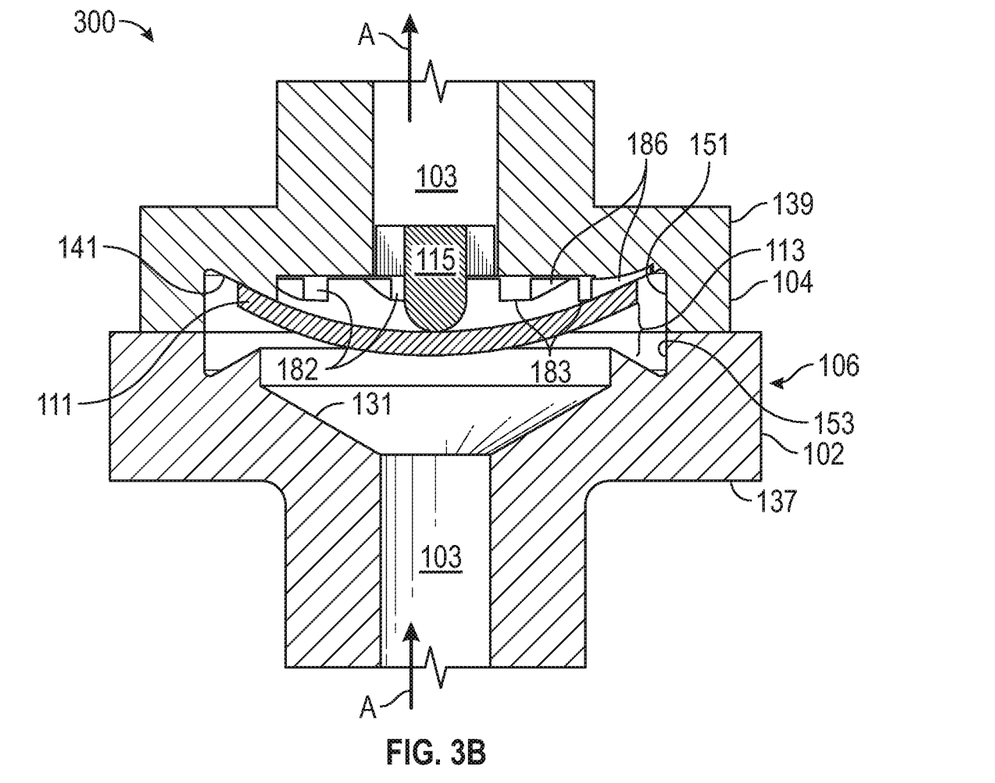

FIGS. 3A and 3B are cross-sectional views of the valve portion 106 of a check valve 300, in accordance with aspects of the present disclosure. FIG. 3A illustrates the check valve 300 in the closed position, wherein the check valve 300 limits (minimizes) fluid flow in the reverse directions, and FIG. 3B illustrates the check valve 300 in the open position, wherein the check valve 300 permits fluid flow in the forward direction.

The check valve 300 may be similar in some respects to the check valves 100 and 200 in FIGS. 1A, 1B, and 2, and therefore may be best understood with reference thereto where like numerals designate like components not described again in detail. For the sake of illustration, the valve portion 106 has been illustrated as inverted.

Referring to FIGS. 3A and 3B, the angled internal surface 141 of the lower housing 104 includes a plurality of projections 182 arranged about the pedestal 115. The projections 182 extend axially and radially around the pedestal 115, which may be located centrally with respect to the passageway 103 in the lower housing 104. Each projection 182 has a curved top surface 183 that is relatively flat and tapers in a radially outward direction. The curvature of the top surface 183 may match the curvature of the valve member 111 when the valve member 111 bends when the check valve 300 is open (See FIG. 3B). Flow channels 186 are formed between adjacent projections 182 and fluid may flow through the flow channels 186 when the check valve 300 is open.

In the closed state illustrated in FIG. 3A, the valve member 111 rests on the projection 132 that may extend into the cavity 121 from the internal surface 131. In more detail, the projection 132 may define a sealing surface 134 at a distal end thereof and the valve member 111 may rest on the sealing surface 134. The projection 132 (and therefore the sealing surface 134) may be disposed in a circular manner about the passageway 103. As illustrated, the projection 132 may be formed by a vertical upstream sidewall 142 and an angled downstream sidewall 144. In the open state illustrated in FIG. 3B, the fluid flow (indicated by arrow A) may cause the valve member 111 to bend about the pedestal 115 and contact the top surface 183 of the projections 182. A gap 113 may be created when the valve member 111 bends and the gap may be wide enough for grit to pass into a lodging space 187 (see below)

Figure 3C:
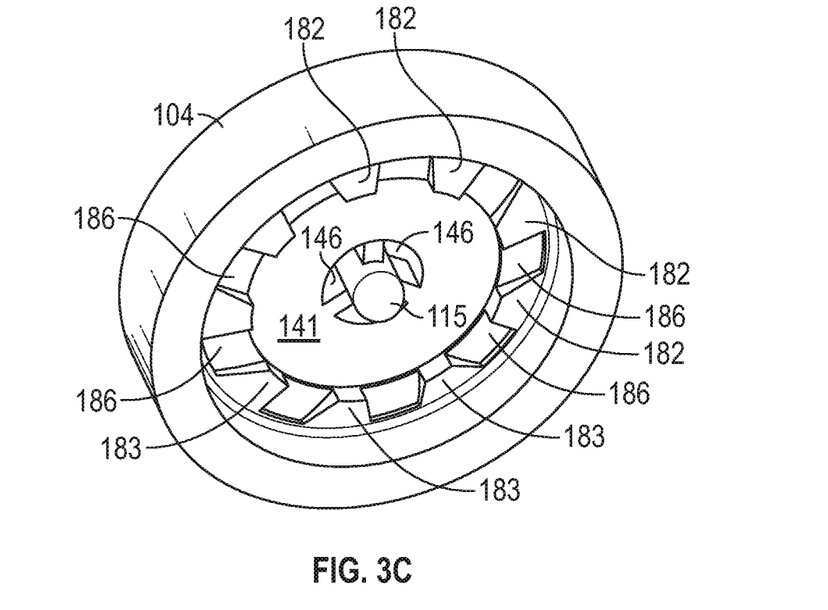
FIG. 3C is a perspective view of the lower housing of the check valve in FIGS. 3A and 3B illustrating the projections and flow channels of in relatively greater detail.

FIG. 3C is a perspective view of the lower housing 104 illustrating the projections 182 and flow channels 186 in relatively greater detail.

Figure 3D:
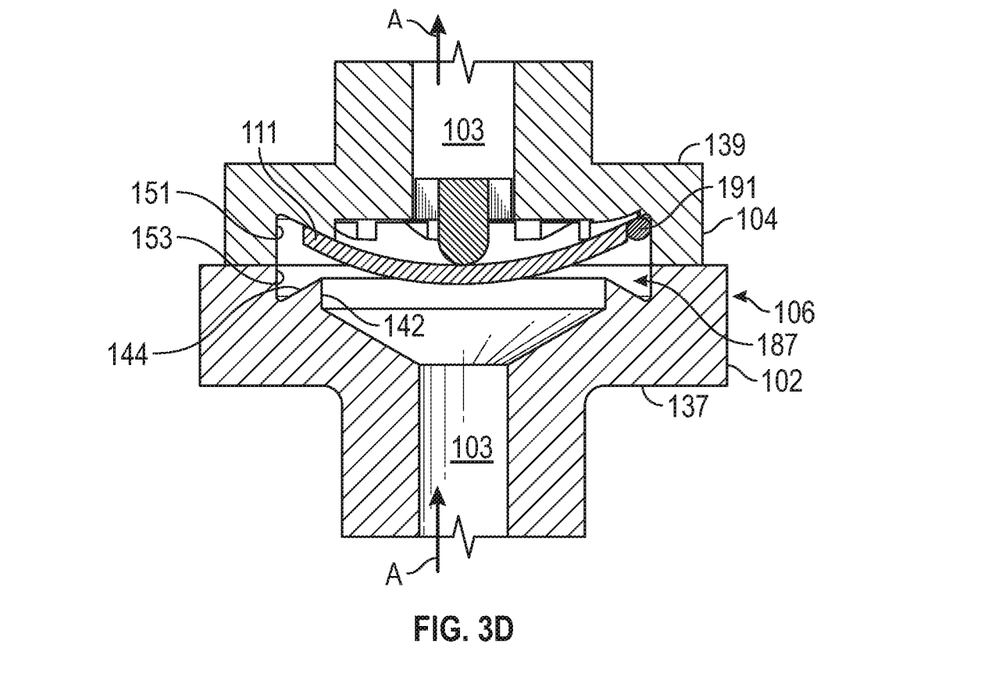
FIGS. 3D and 3E are cross-sectional views of the valve portion of the check valve of FIGS. 3A and 3B illustrating a lodging area of the check valve, in accordance with aspects of the present disclosure.
Figure 3E:
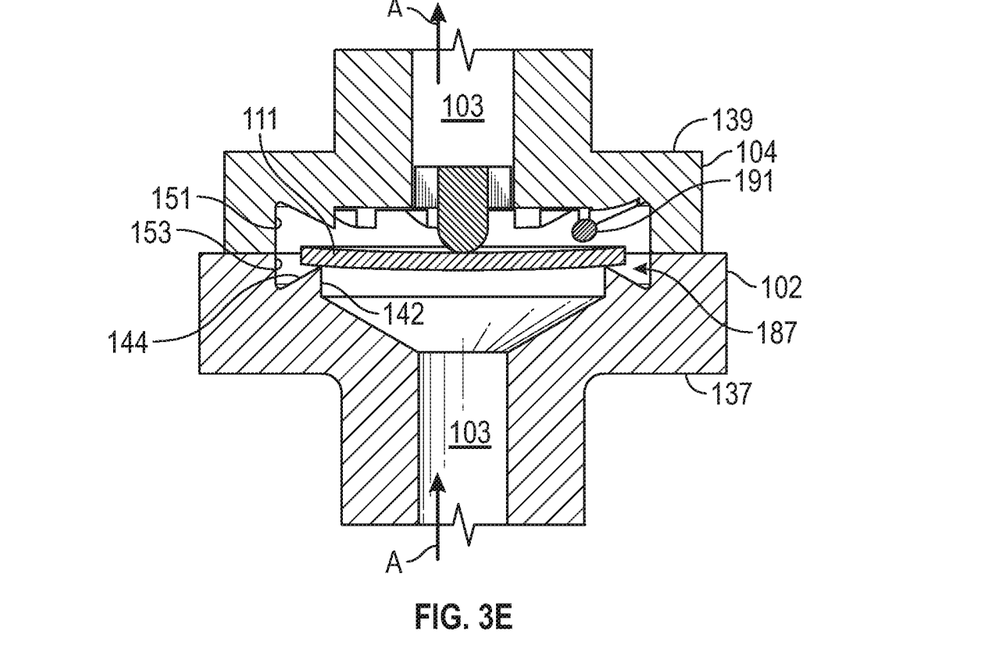

Referring to FIGS. 3D and 3E, a lodging space 187 may be defined co-operatively by the upper housing 102 and the lower housing 104. The lodging space 187 may be located radially outward of the projection 132, and may be or include the radially outermost portion of the cavity 121 (FIG. 3A). The lodging space 187 may be at least partially bounded by the angled internal surface 141 and the downstream sidewall 144, and the internal vertical surfaces 151 and 153. In the open state, grit (or other undesirable particulate matter) 191 may be lodged (or temporarily retained) in the lodging space 187. This is because a relatively greater pressure drop is generated between the flow channels 186 and the outlet 110 which causes the valve member 111 to deflect to a maximum position, wherein the disk surface contacts the top surfaces 183 of the projections 182. The gap 113 (FIG. 3B) between the valve member 111 and the sealing surface 134 is greater than the size of the grit 191 and this may prevent the grit 191 from becoming lodged at the sealing surface 134. If grit 191 becomes lodged, it would be caught only during forward flow condition and would be caught at the entry of the flow channels 186, as illustrated in FIG. 3D. When the forward flow stops and the check valve 300 starts to close (e.g., the valve member 111 moves towards the sealing surface 134), the grit 191 may become dislodged and flow downstream via the flow channels 186. A benefit of this design is that the fluid flow through the check valve 300 is not impeded due to the presence of grit 191 during low flow conditions. Another benefit is that the grit 191 may not be trapped in the gap between the valve member 111 and the projections 182 and "weeping" may be limited.

In an embodiment, the check valve 300 may include the filter 116 arranged in the passageway 103 in the upper housing 102. For instance, referring to FIG. 1B, the array of vertical structures 117 may be arranged in the passageway 103 to filter grit or other undesirable particulate matter and limit the passage thereof into the cavity 121.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1: A check valve, comprising: an upper housing having an inlet of the check valve; a lower housing having an outlet of the check valve; a valve portion formed by the upper and lower housings; a passageway extending between the inlet and outlet; a first filter in the upper housing to limit passage of undesirable matter in fluid flowing through the check valve, the first filter extending axially and radially in the valve portion; and a valve member arranged in the valve portion to selectively permit fluid to flow through the check valve.

Clause 2: The check valve of clause 1, further comprising: a second filter arranged in the passageway to limit passage of undesirable matter in fluid flowing through the check valve, wherein the first filter and the second filter are arranged axially opposite each other in the passageway and including the valve member therebetween.

Clause 3: The check valve of clause 2, wherein the first filter includes an array of vertical structures coupled to the passageway and extending axially and radially in the valve portion, and the second filter includes an array of vertical structures arranged about the passageway and extending axially and radially in the valve portion, the second filter configured to limit passage of undesirable matter in the fluid.

Clause 4: The check valve of clause 1, wherein the lower housing includes a pedestal arranged in the passageway and coupled thereto, one or more flow channels arranged about the pedestal and in fluid communication with the valve portion and the passageway, and the valve member is positioned on the pedestal.

Clause 5: The check valve of clause 1, wherein the upper housing includes a projection disposed in a circular manner about the passageway in the valve portion, a sealing surface is defined at a distal end of the projection, and a gap is defined between the sealing surface and the valve member, the gap limiting passage of undesirable matter.

Clause 6: The check valve of clause 5, wherein the projection includes an upstream sidewall and downstream sidewall, wherein a slope of the upstream sidewall is less than a slope of the downstream sidewall.

Clause 7: The check valve of clause 1, wherein the upper housing defines an opening in fluid communication with the valve portion, and the valve member includes a first end coupled to the lower housing and the upper housing, and a second end opposite the first end and occluding the opening.

Clause 8: The check valve of clause 7, wherein the first end is stationary.

Clause 9: The check valve of clause 7, wherein the lower housing defines a flow channel in fluid communication with the passageway and the valve portion.

Clause 10: The check valve of clause 7, wherein the first filter is arranged about the opening.

Clause 11: The check valve of clause 1, wherein the lower housing includes a plurality of axially and radially extending projections in the valve portion, and a flow channel is defined between adjacent projections, the flow channel being in fluid communication with the passageway and the valve portion.

Clause 12: The check valve of clause 11, wherein the upper housing and the lower housing co-operatively define an internal cavity in the valve portion, and a radially outermost portion of the internal cavity defines a lodging space, the lodging space being radially adjacent the projections and configured to retain the undesirable matter in fluid.

Clause 13: The check valve of clause 11, wherein the plurality of axially and radially extending projections are arranged about the passageway.

Clause 14: A check valve, comprising: an upper housing having an inlet of the check valve; a lower housing axially coupled to the upper housing and having an outlet of the check valve; a valve portion cooperatively formed by the upper and lower housings; a passageway extending between the inlet and outlet; a first filter included in the upper housing to limit passage of undesirable matter in fluid flowing through the check valve; a second filter included in the lower housing to limit passage of undesirable matter in fluid flowing through the check valve, each of the first filter and the second filter including a plurality of vertical structures disposed in the valve portion and extending axially and radially in the valve portion; and a valve member positioned in the valve portion to selectively permit fluid to flow through the check valve.

Clause 15: The check valve of clause 14, wherein an internal surface of the upper housing in the valve portion includes an axially extending projection disposed in a circular manner about the passageway in the valve portion, and a sealing surface is defined at a distal end of the projection, wherein the valve member is configured to contact the sealing surface to limit fluid flow across the sealing surface.

Clause 16: The check valve of clause 14, wherein the plurality of vertical structures are spaced from the valve member.

Clause 17: A check valve, comprising: an upper housing having an inlet of the check valve; a lower housing axially coupled to the upper housing and having an outlet of the check valve; a valve portion cooperatively formed by the upper and lower housings; a passageway extending between the inlet and outlet; and a valve member arranged in the valve portion to selectively permit fluid to flow through the check valve, wherein the upper housing defines an opening in fluid communication with the valve portion, and the valve member is elongated and has a first end coupled to the lower housing and the upper housing, and a second opposite end occluding the opening.

Clause 18: The check valve of clause 17, wherein an internal surface of the lower housing in the valve portion defines a flow passage in fluid communication with the valve portion and the passageway.

Clause 19: The check valve of clause 17, wherein a filter is arranged about the opening.

Clause 20: A check valve, comprising: an upper housing having an inlet of the check valve; a lower housing axially coupled to the upper housing and having an outlet of the check valve; a valve portion formed by the upper and lower housings; a passageway extending between the inlet and outlet; and a valve member arranged in the valve portion to selectively permit fluid to flow through the check valve, wherein the lower housing includes a plurality projections extending of axially and radially from an internal surface of the lower housing in the valve portion, a flow channel is defined between adjacent projections, the flow channel being in fluid communication with the passageway and the valve portion, and the upper housing and the lower housing co-operatively define an internal cavity in the valve portion, and a radially outermost portion of the internal cavity defines a lodging space configured to retain undesirable matter in fluid.

Clause 21: The check valve of clause 20, wherein a filter is arranged in the passageway in the upper housing.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A check valve, comprising:
    an upper housing having an inlet of the check valve;
    a lower housing having an outlet of the check valve;
    a valve portion formed by the upper and lower housings, wherein the valve portion defines an internal cavity;
    a passageway extending between the inlet and outlet;
    a first filter in the upper housing to limit passage of undesirable matter in fluid flowing through the check valve, the first filter extending axially and radially in the valve portion;
    a valve member arranged in the valve portion to selectively permit fluid to flow through the check valve;
    a pedestal coupled to an internal sidewall of the lower housing, wherein the pedestal extends into the internal cavity and the pedestal supports the valve member; and
    at least one channel defined between the internal sidewall and the pedestal, wherein the at least one channel is in fluid communication with the passageway.

2. The check valve of claim 1, further comprising:
a second filter arranged in the passageway to limit passage of undesirable matter in fluid flowing through the check valve, wherein
the first filter and the second filter are arranged axially opposite each other in the passageway and including the valve member therebetween.

3. The check valve of claim 2, wherein
the second filter includes an array of vertical structures arranged about the passageway and extending axially and radially in the valve portion, the second filter configured to limit passage of undesirable matter in the fluid.

4. The check valve of claim 1, wherein the upper housing includes a projection disposed in a circular manner about the passageway in the valve portion,
a sealing surface is defined at a distal end of the projection, and
a gap is defined between the sealing surface and the valve member, the gap limiting passage of undesirable matter.

5. The check valve of claim 4, wherein the projection includes an upstream sidewall and downstream sidewall, wherein a slope of the upstream sidewall is less than a slope of the downstream sidewall.

6. The check valve of claim 1, wherein the upper housing defines an opening in fluid communication with the valve portion, and
the valve member includes a first end coupled to the lower housing and the upper housing, and a second end opposite the first end and occluding the opening.

7. The check valve of claim 6, wherein the first end is stationary.

8. The check valve of claim 6, wherein the lower housing defines a flow channel in fluid communication with the passageway and the valve portion.

9. The check valve of claim 6, wherein the first filter is arranged about the opening.

10. The check valve of claim 1, wherein the lower housing includes a plurality of axially and radially extending projections in the valve portion, and
a flow channel is defined between adjacent projections, the flow channel being in fluid communication with the passageway and the valve portion.

11. The check valve of claim 10, wherein the upper housing and the lower housing co-operatively define an internal cavity in the valve portion, and a radially outermost portion of the internal cavity defines a lodging space, the lodging space being radially adjacent the projections and configured to retain undesirable matter in fluid.

12. The check valve of claim 10, wherein the plurality of axially and radially extending projections are arranged about the passageway.

13. A check valve, comprising:
an upper housing having an inlet of the check valve;
a lower housing axially coupled to the upper housing and having an outlet of the check valve;
a valve portion cooperatively formed by the upper and lower housings, wherein the valve portion defines an internal cavity;
a passageway extending between the inlet and outlet;
a first filter included in the upper housing to limit passage of undesirable matter in fluid flowing through the check valve;
a second filter included in the lower housing to limit passage of undesirable matter in fluid flowing through the check valve;
a valve member positioned in the valve portion to selectively permit fluid to flow through the check valve;
a pedestal coupled to an internal sidewall of the lower housing, wherein the pedestal extends into the internal cavity and the pedestal supports the valve member; and
a plurality of channels defined between the internal sidewall and the pedestal, wherein the plurality of channels is in fluid communication with the passageway.

14. The check valve of claim 13, wherein an internal surface of the upper housing in the valve portion includes an axially extending projection disposed in a circular manner about the passageway in the valve portion, and
a sealing surface is defined at a distal end of the projection, wherein the valve member is configured to contact the sealing surface to limit fluid flow across the sealing surface.

15. A check valve, comprising:
an upper housing having an inlet of the check valve;
a lower housing axially coupled to the upper housing and having an outlet of the check valve;
a valve portion cooperatively formed by the upper and lower housings;
a passageway extending between the inlet and outlet, wherein the valve portion defines an internal cavity;
a valve member arranged in the valve portion to selectively permit fluid to flow through the check valve, wherein the upper housing defines an opening in fluid communication with the valve portion, wherein a filter is arranged about the opening, the filter including a plurality of vertical structures at least partially disposed in the passageway, and the valve member is elongated and has a first end coupled to the lower housing and the upper housing, and a second opposite end occluding the opening;
a pedestal coupled to an internal sidewall of the lower housing, wherein the pedestal extends into the internal cavity and the pedestal supports the valve member; and
at least one channel defined between the internal sidewall and the pedestal, wherein the at least one channel is in fluid communication with the passageway.

16. The check valve of claim 15, wherein an internal surface of the lower housing in the valve portion defines a flow passage in fluid communication with the valve portion and the passageway.

17. A check valve, comprising:
an upper housing having an inlet of the check valve;
a lower housing axially coupled to the upper housing and having an outlet of the check valve;
a valve portion formed by the upper and lower housings, wherein the valve portion defines an internal cavity;
a passageway extending between the inlet and outlet;
a valve member arranged in the valve portion to selectively permit fluid to flow through the check valve, wherein a flow channel is defined between adjacent projections, the flow channel being in fluid communication with the passageway and the valve portion, and the upper housing and the lower housing co-operatively define an internal cavity in the valve portion, and a radially outermost portion of the internal cavity defines a lodging space configured to retain undesirable matter in fluid;
a pedestal coupled to an internal sidewall of the lower housing, wherein the pedestal extends into the internal cavity and the pedestal supports the valve member at a center of the valve member; and at least one channel defined between the internal sidewall and the pedestal, wherein the at least one channel is in fluid communication with the passageway.

18. The check valve of claim 17, wherein a filter is arranged in the passageway in the upper housing.

* * * * *